US008220341B2

(12) United States Patent
David et al.

(10) Patent No.: US 8,220,341 B2
(45) Date of Patent: Jul. 17, 2012

(54) METHOD AND DEVICE FOR ANALYZING A MULTIPLE-PHASE FLUID BY MEASURING ADMITTANCE USING COAXIAL PROBES

(75) Inventors: Pierre-Yves David, Jouy le Moutier (FR); Bruno Le Briere, Paris (FR); Arlette Fourrier-Lamer, Les Lilas (FR); Olivier Dubrunfaut, Palaiseau (FR); Jean-Claude Badot, Paris (FR); Emmanuel Bondet De La Bernardie, Toulon (FR)

(73) Assignees: Geoservices Equipements, Roissy en France (FR); Centre National de la Recherche Scientifique (C.N.R.S.), Paris (FR); Ecole Superieure d'Electricite (Supelec), Cedex (FR)

( * ) Notice: Subject to any disclaimer, the term of this patent is extended or adjusted under 35 U.S.C. 154(b) by 435 days.

(21) Appl. No.: 12/310,800

(22) PCT Filed: Sep. 5, 2007

(86) PCT No.: PCT/FR2007/001436
§ 371 (c)(1),
(2), (4) Date: Nov. 25, 2009

(87) PCT Pub. No.: WO2008/029025
PCT Pub. Date: Mar. 13, 2008

(65) Prior Publication Data
US 2010/0064820 A1    Mar. 18, 2010

(30) Foreign Application Priority Data
Sep. 8, 2006   (FR) .................................... 06 07887

(51) Int. Cl.
*G01F 1/74*   (2006.01)
*G01G 11/00*  (2006.01)

(52) U.S. Cl. ........................................ 73/861.04; 702/50
(58) Field of Classification Search .................... None
See application file for complete search history.

(56) References Cited

U.S. PATENT DOCUMENTS
2003/0011386 A1    1/2003   Xie et al.
(Continued)

FOREIGN PATENT DOCUMENTS
WO    WO 99/42794    8/1999

OTHER PUBLICATIONS
International Search Report issued Jan. 21, 2008 in the International Application No. PCT/FR2007/001436.
(Continued)

*Primary Examiner* — Harshad R Patel
(74) *Attorney, Agent, or Firm* — Wenderoth, Lind & Ponack, L.L.P.

(57) ABSTRACT

A method and device includes measuring a multiple-phase fluid flowing through a pipe. The inventive method includes the following steps in which: a fluid is illuminated using a first coaxial probe placed in contact with the liquid phase of the fluid, and a first electromagnetic wave is emitted at a high frequency. The admittance at the interface between the first probe and the fluid is measured, and the fractions of at least two constituents of the liquid phase are calculated in order to obtain the effective permittivity ($\epsilon_1$) of the phase. The method also includes the following steps in which: the fluid is illuminated using a second coaxial probe and a second electromagnetic wave is emitted at a low frequency. The admittance at the interface between the second probe and the liquid is measured, and the thickness (e) of the liquid is measured. The aforementioned calculation is performed on the basis of the calculated effective permittivity ($\epsilon_1$) and the admittance measured by the second probe.

23 Claims, 5 Drawing Sheets

U.S. PATENT DOCUMENTS

2008/0183392 A1* 7/2008 Forgang .......................... 702/12
2009/0126502 A1* 5/2009 Wee et al. .................. 73/861.04
2009/0204346 A1* 8/2009 Xie ................................ 702/45
2011/0138928 A1* 6/2011 Xie et al. ................... 73/861.04

OTHER PUBLICATIONS

Jannicke Hilland, "Simple Sensor System for Measuring the Dielectric Properties of Saline Solutions," Measurement Science and Technology, Institute of Physics Publishing, Bristol, GB, vol. 8, No. 8, pp. 901-910, Aug. 1997.

Kjetil Folgero et al., "Permittivity Measurement of Thin Liquid Layers Using Open-Ended Coaxial Probes," Measurement Science and Technology, Institute of Physics Publishing, Bristol, GB, vol. 7, No. 8, pp. 1164-1173, Aug. 1996.

* cited by examiner

METHOD AND DEVICE FOR ANALYZING A MULTIPLE-PHASE FLUID BY MEASURING ADMITTANCE USING COAXIAL PROBES

BACKGROUND OF THE INVENTION

The present invention relates to a method for measuring (analyzing) a multiple-phase fluid flowing through a pipe, the fluid comprising a liquid phase in contact with a surface of the pipe and a gas phase located away from the surface covered by the liquid.

In order to optimize the production and lifetime of hydrocarbon producing operations, it is known to use a multiple-phase flow meter which allows the proportions of liquid and gas in a pipe of the installation, for example located at the outlet of a production well, to be determined regularly.

The data supplied by the measurement are used by the operators of the installation, especially in order to adapt the separation conditions of the phases of the multiple-phase fluid.

To that end, the flow-rate measurement has to be accurate (plus or minus 5% of the flow rate for each phase), non-destructive, reliable and independent of the type of flow regime flowing through the pipe.

In order to measure the phase fractions, it is known to use an instrument employing a radioactive source, which has a number of disadvantages in terms of storage, transportation and use.

In order to overcome that problem, there is known from the article by Hilland in Meas. Sci. Technol. 8 (1997) pages 901 to 910 a method for measuring a multiple-phase fluid flowing through a pipe with the aid of a coaxial probe, the end of which is placed in contact with the fluid.

The fluid is illuminated by the coaxial probe with the aid of an electromagnetic wave, and the admittance is measured at the interface between the probe and the fluid. The permittivity of the fluid and its composition are then calculated.

In order to operate the system, it is necessary to calibrate the probe with the aid of at least three reference solutions and then use an empirical model. The accuracy of the measurement is therefore not wholly satisfactory.

SUMMARY OF THE INVENTION

An object of the invention is, therefore, to obtain a method for analyzing a multiple-phase fluid which allows at least the proportions of each of the constituents of the multiple-phase fluid to be measured by a simple and very accurate method.

To that end, the invention relates to a method of the above-mentioned type, characterized in that it comprises the following steps:

(a) determination of the relative fractions of at least two constituents of the liquid phase, comprising the following phases:
  illumination of the fluid by a first coaxial probe placed in contact with the liquid phase, with a first electromagnetic wave emitted at a high frequency;
  measurement of the admittance at the interface between the first probe and the fluid; and
  calculation of the relative fractions on the basis of the measured admittance;
(b) determination of the thickness of the liquid phase, comprising the following phases:
  calculation of the effective permittivity of the liquid phase on the basis of the relative fractions calculated in step (a); and
  illumination of the fluid by a second coaxial probe separate from the first probe, with a second electromagnetic wave emitted at a low frequency;
  measurement of the admittance at the interface between the second probe and the fluid; and
  calculation of the thickness of the liquid phase on the basis of the calculated effective permittivity of the liquid phase, and of the admittance measured at the interface between the second probe and the fluid.

The method according to the invention can have one or more of the following features, taken in isolation or according to all technically possible combinations.

The first coaxial probe can comprise a central core which extends radially relative to an axis of the pipe, and a cylindrical solid dielectric window which has a first face in contact with the fluid and a second face in contact with the central core, the first electromagnetic wave being emitted through the dielectric window.

The phase of calculation of the relative fractions in the liquid phase can comprise the establishment of a correlation between:
  a simulated admittance at the interface between the first probe and a reference fluid and
  the relative fractions in that reference fluid, on the basis of a finite element simulation of the propagation of the first wave in the reference fluid.

The high frequency can give greater than 25 GHz and is preferably from 30 GHz to 60 GHz. The second coaxial probe can have a central core which extends radially relative to an axis of the pipe, and a cylindrical solid dielectric window which has a first face in contact with the fluid and a second face in contact with the central core.

The low frequency can be below 1 GHz.

The phase of calculation of the thickness of the liquid phase can comprise the use of an equation which links:
  a theoretical admittance calculated at an interface between the second probe and a theoretical calculation cell having a finite radial length and a geometry different from that of the pipe, to:
  the effective permittivity of the liquid phase, and
  the radial length, the equation being obtained on the basis of the analytical resolution of a mathematical model of propagation of the second wave in the theoretical calculation cell.

The phase of calculation of the thickness can comprise the following subsidiary steps:
  variation of the radial length of the theoretical calculation cell;
  calculation of the difference between the admittance calculated on the basis of the mathematical model of propagation in the calculation cell at the interface between the second probe and the fluid, and the admittance measured in step (b); and
  determination of the thickness of the liquid phase on the basis of the radial length of the calculation cell obtained when the difference is below a predetermined value.

The calculation cell can be formed by a closed hollow metal cylinder whose radial axis is coaxial with the axis of the central core of the second probe, the cylinder having a first transverse wall located at the interface between the second probe and the pipe, the radial length being the distance separating the first transverse wall and a second transverse wall delimiting the cylinder.

The invention relates further to a device for measuring a multiple-phase fluid flowing through a pipe, the fluid comprising a liquid phase in contact with a surface of the pipe and a gas phase located away from the surface covered by the liquid, the device comprising:

(a) means for determining the relative fractions of the constituents of the liquid phase, comprising:

a first coaxial probe which is placed in contact with the liquid phase and is capable of emitting a first electromagnetic wave at a high frequency;

first means for measuring the admittance at the interface between the first probe and the fluid;

first means for calculating the relative fractions in the liquid phase on the basis of the measured admittance;

(b) means for determining the thickness of the liquid phase, comprising:

means for calculating the effective permittivity on the basis of the relative fractions calculated by the first means for calculating the composition; and a second coaxial probe, separate from the first probe, which is capable of emitting a second electromagnetic wave at a low frequency;

second means for measuring the admittance at the interface between the second probe and the fluid;

second means for calculating the thickness of the liquid phase on the basis of the effective permittivity calculated by the means for calculating the permittivity, and of the admittance measured by the second measuring means.

The device according to the invention can have one or more of the following features, taken in isolation or according to all technically possible combinations.

The first coaxial probe can comprise a central core which extends radially relative to an axis of the pipe, and a cylindrical solid dielectric window having a first face which is to come into contact with the fluid and a second face in contact with the central core.

The second coaxial probe can have a central core which extends radially relative to an axis of the pipe, and a cylindrical solid dielectric window having a first face which is to come into contact with the fluid and a second face in contact with the central core.

The means for determining the thickness can comprise means for using an equation which links:

a theoretical admittance calculated at an interface between the second probe and a theoretical calculation cell having a finite radial length and a geometry different from that of the pipe, to:

the effective permittivity of the liquid phase and the radial length, the equation being obtained on the basis of the analytical resolution of a mathematical model of propagation of the second wave in the theoretical calculation cell.

BRIEF DESCRIPTION OF THE DRAWINGS

The invention will be better understood from reading the following description, which is given solely by way of example and with reference to the accompanying drawings, in which.

DETAILED DESCRIPTION OF THE INVENTION

Figure 2:
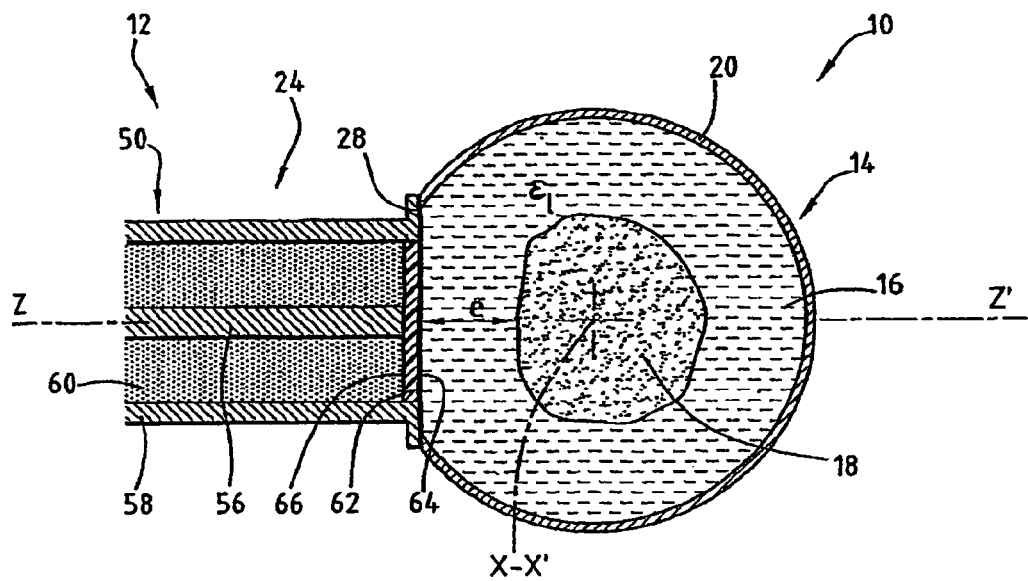
FIG. 2 is a cutaway view according to the horizontal plane II of the device of FIG. 1.
Figure 3:
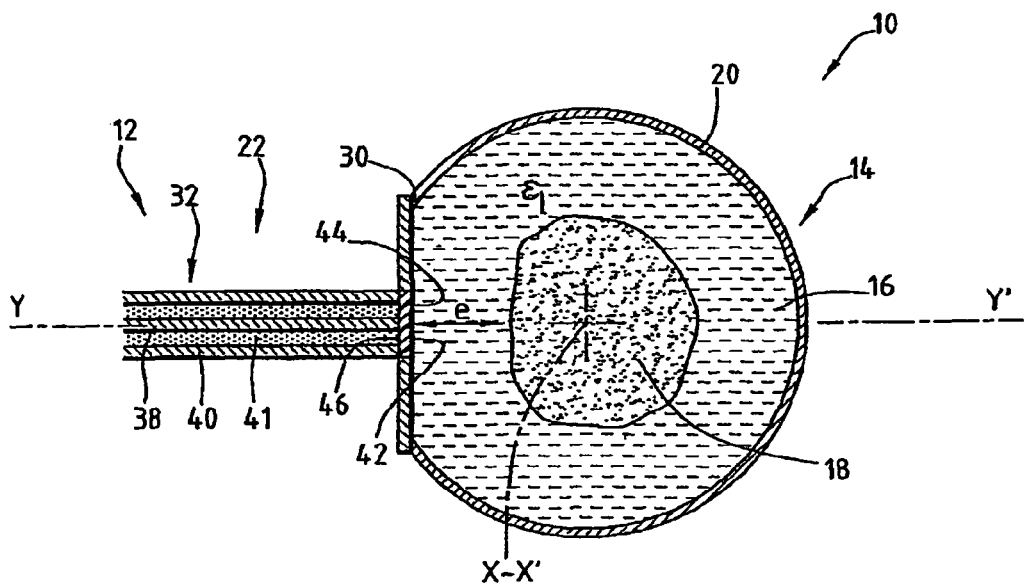
FIG. 3 is a cutaway view according to the horizontal plane III of the device of FIG. 1.

The analyzing method according to the invention is to be carried out in an installation for extraction of a multiple-phase fluid, such as a hydrocarbon extraction installation 10. The method is carried out with the aid of a device 12 shown in FIGS. 1 to 3.

Figure 1:
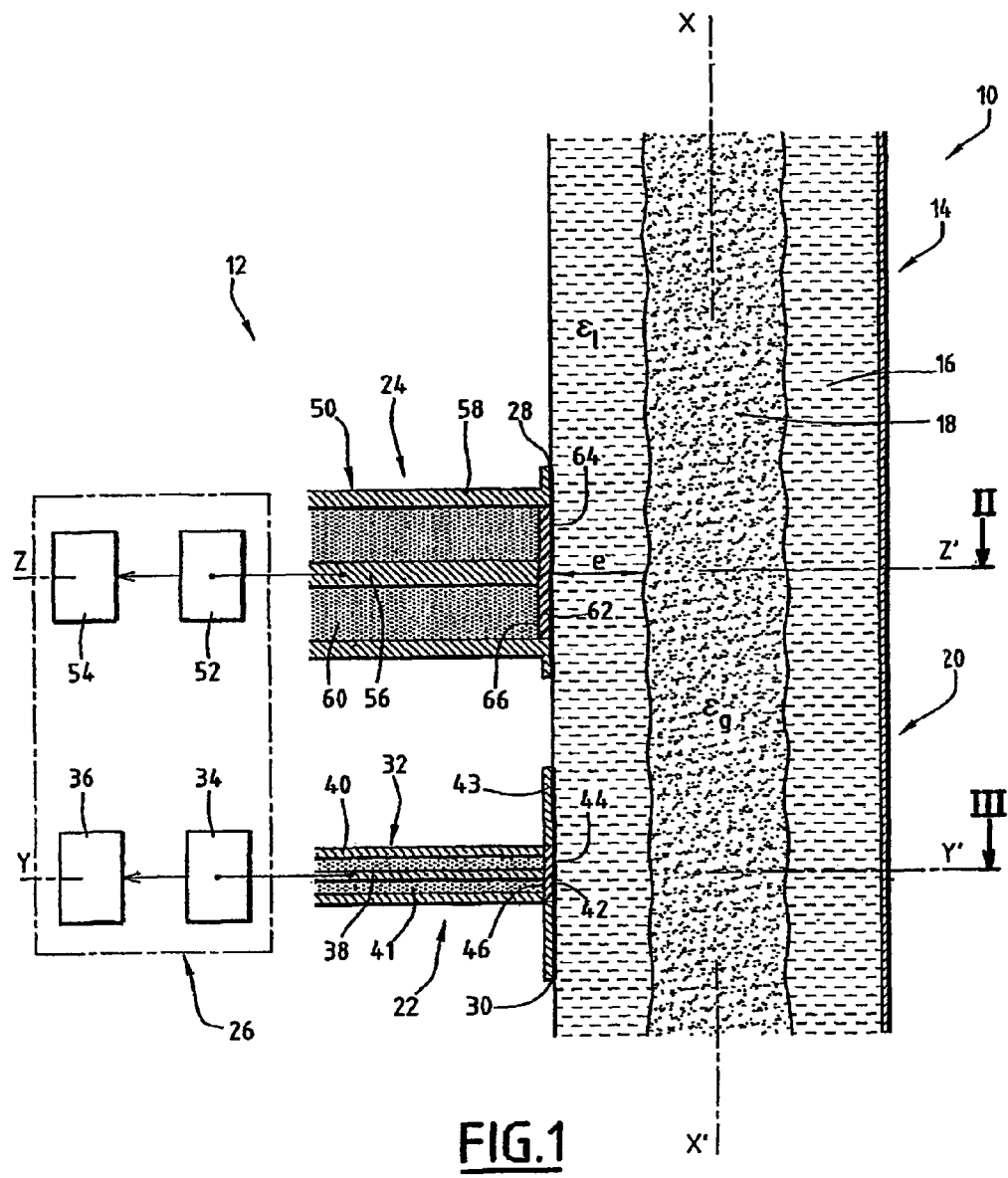
FIG. 1 is a cutaway view, in diagrammatic form, according to a vertical plane, of a device for carrying out a method according to the invention.

In a known manner, the installation 10 comprises, for example, an extraction well (not shown) formed underground, and a pipe 14, shown in FIG. 1, which connects the well to an assembly for storing the extracted hydrocarbons (not shown).

In the example shown in FIG. 1, the pipe 14 is a substantially cylindrical and vertical pipe. The pipe 14 forms, for example, part of a multiple-phase flow meter capable of measuring the flow rate of hydrocarbons flowing through the pipe 14.

The multiple-phase fluid flows in the pipe in the form of a liquid phase 16, which is formed by an oil-in-water or water-in-oil emulsion, and a gas phase 18.

The liquid phase 16 flows along the walls of the pipe 14 in the form of an annular sleeve of average thickness e, which covers substantially the whole of the inside surface of the pipe 14.

The gas phase 18 flows substantially in the center of the liquid phase 16, along an axis X-X' of the pipe.

The liquid phase 16 has an effective permittivity $\in_l$ which is different from that of the gas phase $\in_g$.

The device 12 comprises a measuring cell 20, means 22 for determining the composition of the liquid phase 16, means 24 for determining the thickness e of the liquid phase 18, and a computer 26.

The expression "composition of the liquid phase" is understood as meaning the relative fractions by volume of at least two constituents of the liquid phase, that is to say, in this example, water and oil, and optionally an emulsion.

The measuring cell 20 is formed by a portion of the vertical pipe 14 delimiting an upper opening 28 and a lower opening 30.

Each opening 28, 30 is delimited laterally by two generatrices of the cylinder constituting the pipe 14 that are located in a vertical plane.

The means 22 for determining the composition comprises a high-frequency coaxial probe 32, one end of which is placed radially in contact with the liquid phase 16, means 34 for measuring the admittance at the interface between the liquid phase 16 and the probe 32, and means 36 for calculating the composition.

The probe 32 is produced in the form of a standard APC 2.4 type connection. It comprises a central conductive core 38, an outer conductive jacket 40, and an annular insulator 41 located between the central core 38 and the jacket 40.

The high-frequency probe 32 further comprises a cylindrical solid dielectric window 42 in contact with the liquid phase 16.

The core 38, the insulator 41 and the jacket 40 extend close to the lower opening 30 according to a substantially radial axis Y-Y'. The outside diameter of the core 38 about the axis Y-Y' is 1.04 mm and the inside diameter of the jacket 40 about the axis Y-Y' is 2.4 mm.

The jacket 40 is extended at the lower end of the probe 32 by a collar 43 for closing off the lower opening 30.

The window 42 is based on PEEK. It has a thickness greater than 0.7 mm and substantially equal to 1 mm, between a flat inner face 44 in contact with the liquid phase 16 and a flat outer face 46 placed in contact with the core 38 and the insulator 41, in order to ensure good mechanical strength and good tightness.

The faces 46 and 44 are perpendicular to the radial axis Y-Y'. Accordingly, the window 42 closes off the probe 32 at its inner end towards the axis X-X' and ensures tightness between the inside of the pipe 14 and the probe 32. In addition, the inner face 44 is flush with the wall of the pipe 14.

The means for measuring the admittance 34 and the calculation means 36 are located in the computer 26. They are connected to the high-frequency probe 32.

The means 24 for determining the thickness comprises a low-frequency coaxial probe 50, one end of which is placed radially in contact with the liquid phase 16, means 52 for measuring the admittance at the interface between the liquid phase 16 and the probe 50, and means 54 for calculating the permittivity $\in_1$ of the liquid phase and the thickness e.

The low-frequency probe 50 is produced according to the standard GR 900 connection. It thus extends radially relative to the axis X-X' of the pipe 14, parallel to an axis Z-Z', above the high-frequency probe 32.

The low-frequency probe 50 comprises a conductive central core 56 of axis Z-Z' close to the upper opening 28, a conductive outer jacket 58, and an annular insulator 60 interposed between the jacket 58 and the central core 56.

The probe 50 further comprises a solid cylindrical dielectric window 62 at its end in contact with the liquid phase 16.

The inside diameter of the central core 56 about the axis Z-Z' is substantially equal to 6.20 mm, while the inside diameter of the jacket 58 is 14.28 mm. The inner end of the central core 56 is placed in contact with the liquid phase 16.

The cylindrical window 62 is produced on the basis of PEEK. It extends around the core 56 at the inner end of the probe 50. The cylindrical window 62 accordingly has an inner face 64 in contact with the liquid phase, and an outer face 66 in contact with the central core 56.

The core 56 and the inner face 64 of the window 62 thus isolate the low-frequency probe 50 relative to the inside of the pipe 14 by closing off the upper opening 28 in a tight manner.

The measuring means 52 and the calculation means 54 are located in the computer 36. They are connected to the low-frequency probe 50.

The diameter of the collar 43 of the high-frequency probe 32 is substantially equal to the diameter of the low-frequency probe 50.

The method for measuring the multiple-phase fluid flowing through the pipe 14 will now be described in relation to FIGS. 4 to 7.

In the following, the admittance at an interface is defined as the ratio $$Y = \frac{1-\Gamma}{1+\Gamma},$$

where $\Gamma$ is the complex reflection coefficient of an electromagnetic wave at the interface.

Figure 4:
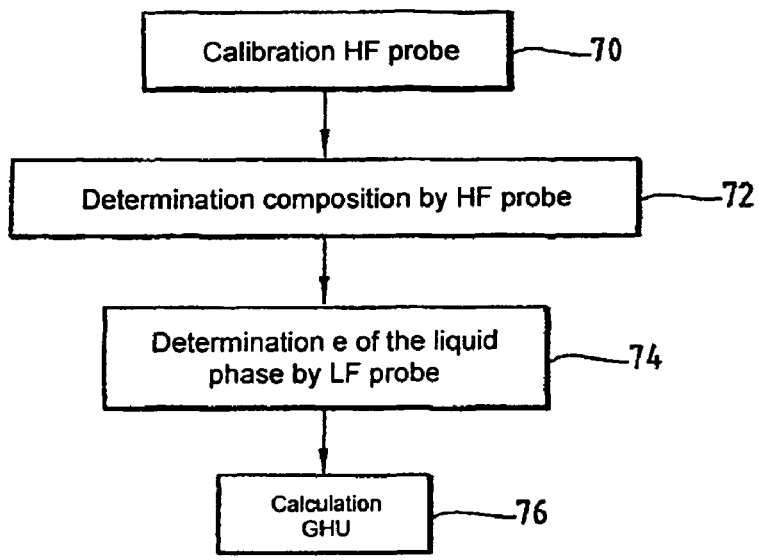
FIG. 4 is a flow chart describing the principal steps of the method according to the invention.

As is shown by FIG. 4, the method first comprises a step 70 of simulation of the propagation in the pipe 14 of a wave emitted by the high-frequency probe 32 in order to establish a correlation between the composition of the liquid phase and the admittance measured at the interface 44 between the high-frequency probe 32 and the liquid phase 16. The method then comprises a step 72 of determination of the composition of the liquid phase 16 by the high-frequency probe 32, a step 74 of determination of the thickness e of the liquid phase 16 by the low-frequency probe 50, and a step 76 of calculation of the gas hold-up (GHU), which is the proportion of gas in the cross-section of the pipe 14.

In the simulation step 70, the admittance at the interface between the window 42 and a reference liquid is simulated with the aid of finite element simulation software, such as the ANSYS Multiphysics software from ANSYS, for at least one given illumination frequency $f_h$ of the reference liquid by the high-frequency probe. The composition of the reference liquid constituted by water and oil is varied from a fraction by volume of water of zero to a fraction by volume of water equal to 1.

The given illumination frequency $f_h$ is, for example, from 20 GHz to 60 GHz, preferably 32 GHz. At that frequency, and taking into consideration the geometry of the high-frequency coaxial probe 32, and especially of the cylindrical dielectric window 42, the penetration of the electromagnetic wave emitted by the probe 32 into the liquid phase 16 is reduced to a very fine layer of liquid applied to the window 42. The presence of the gas phase 18 does not affect the value of the measured admittance.

For the simulation, the pipe 14 is therefore regarded as being filled completely with the liquid phase 16.

Furthermore, given the frequency range in which the high-frequency coaxial probe 32 is used, the conductivity of the aqueous phase no longer affects the permittivity of the water at those frequencies and has therefore been disregarded.

A substantially linear reference curve linking the imaginary component of the simulated admittance to the fraction by volume of water in the reference liquid is thus established at the given frequency, for example 32 GHz.

Figure 5:
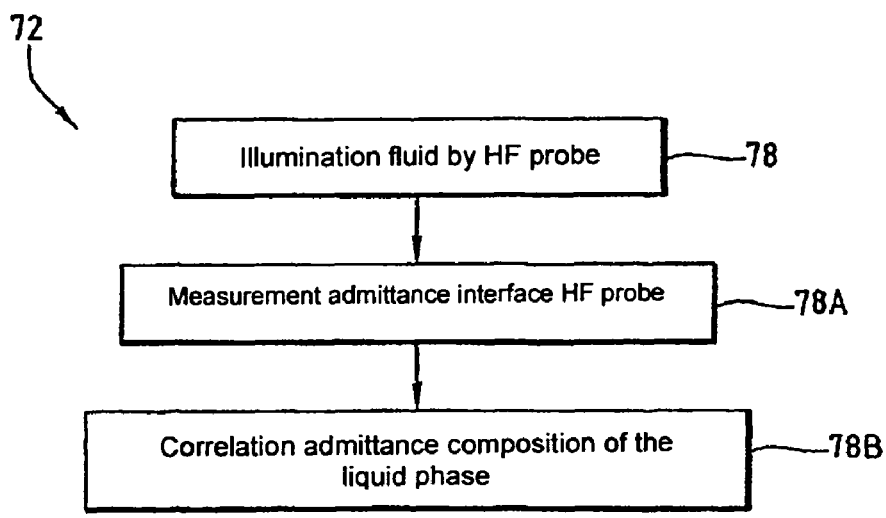
FIG. 5 is a flow chart describing the details of the step of determining the composition of the liquid phase in the method of FIG. 4.

Then, as is illustrated by FIG. 5, the step 72 of determination of the composition of the liquid phase 16 is carried out.

Step 72 comprises the illumination 78 of the multiple-phase fluid with a first electromagnetic wave emitted at a high frequency equal to the frequency $f_h$ used in the simulation step 70, followed by measurement 78A of the admittance at the interface between the high-frequency probe 32 and the liquid phase 16 by the measuring means 34. Step 72 further comprises the correlation 78B between the admittance measured by the measuring means 34 and the composition of the liquid phase 16.

In that frequency range, the wave emitted by the probe 32 is evanescent in the liquid phase 16.

The correlation 78B between the admittance measured in step 78A and the composition of the liquid phase 16 is effected with the aid of the reference curve obtained in the simulation step 70, by determining, according to that curve, the value of the fraction by volume of water of the liquid phase 16 corresponding to the imaginary component of the admittance measured by the measuring means 34.

The step 74 of determination of the thickness e of the liquid phase 16 by the low-frequency probe 50 is then carried out. Step 74 is described in FIG. 6. This step first comprises a phase 78C of calculation of the effective permittivity $\in_1$ of the liquid phase 16 solely on the basis of the composition of the aqueous phase 16 as calculated in step 72.

The calculation 78C of the effective permittivity $\in_1$ comprises the use of a law of mixture based on the fraction by volume of water determined in phase 78B, optionally accompanied by a salinity model as described in the article by J. Hilland, Simple sensor system for measuring the dielectric properties of saline solutions, Meas. Sci. Technol (8) pp. 901-910, 1997, and a Debye model as described in the article by P. Debye, Polar molecules, Chemical Catalog Company, New York, 1929.

Step 74 then comprises a phase 80 of illumination of the multiple-phase fluid by means of the low-frequency probe 50 with the aid of a second electromagnetic wave at a low frequency $f_b$, which is lower than the high frequency, of, for example, from 1 MHz to 1000 MHz, and then a phase of measurement 82 of the admittance $Y_m$ at the interface between the low-frequency probe 50 and the liquid phase 16 by the measuring means 52.

In this frequency range, the second electromagnetic wave emitted by the low-frequency probe 50 is evanescent. It penetrates into the liquid phase 16 and propagates as far as the gas phase 18.

Figure 7:
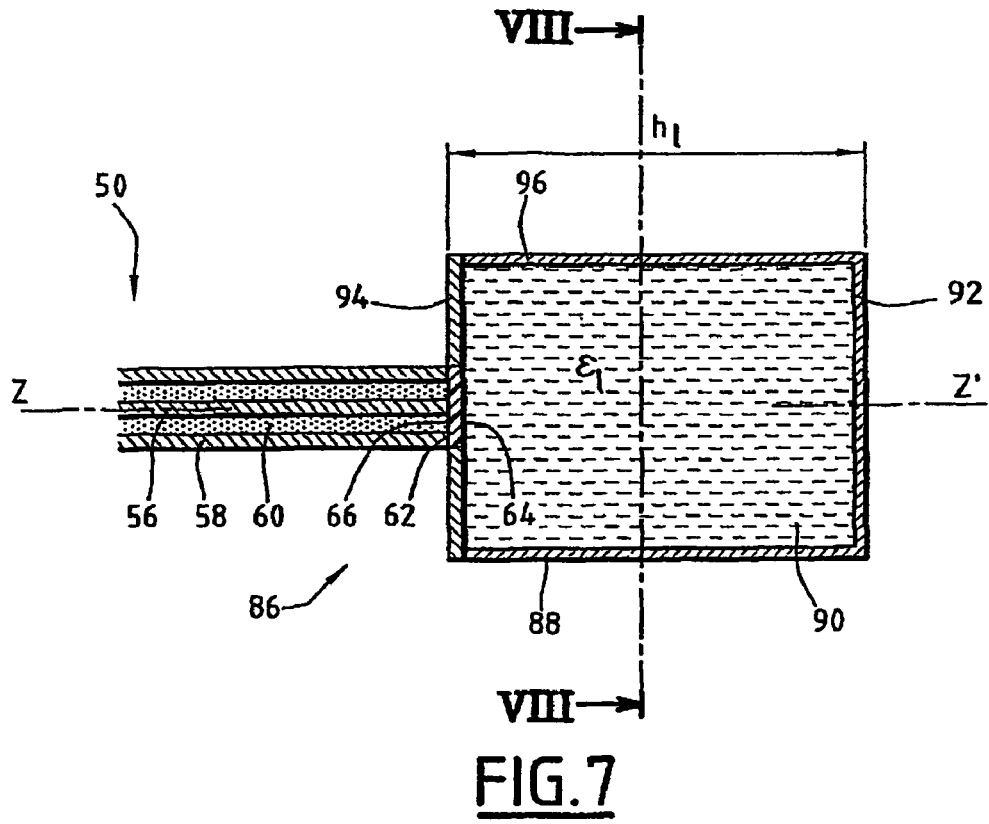
FIG. 7 is a partially cutaway view, in diagrammatic form, according to a median longitudinal plane, of the theoretical calculation cell of the mathematical model of propagation used in the method according to the invention.
Figure 8:
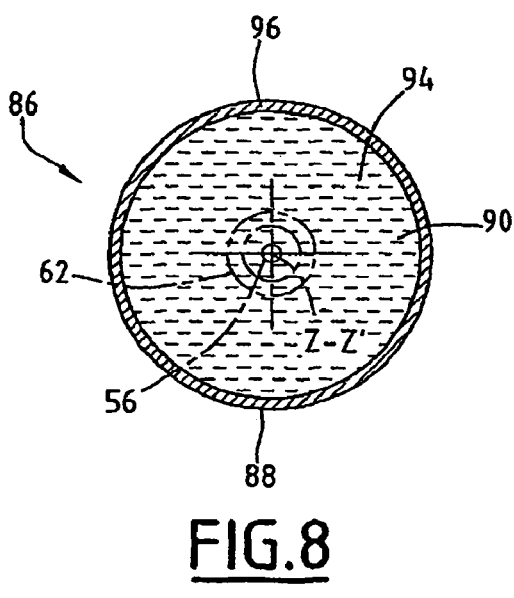
FIG. 8 is a cutaway view according to a transverse plane of the cell of FIG. 7.

Step 74 further comprises a phase 84 of calculation of the thickness e, on the basis of the effective permittivity $\in_1$ determined in step 78C by means of the composition of the aqueous phase 16 calculated in step 72, of the admittance $Y_m$ measured in phase 82 by the measuring means 52, and of a resolved mathematical model of propagation of the second electromagnetic wave in a theoretical calculation cell 86 shown in FIGS. 7 and 8.

As is shown by FIGS. 7 and 8, the cell 86 has a geometry which is different from that of the pipe 14. The cell 86 is virtually formed by a closed metal wall 88 which delimits an inner volume 90 filled with the liquid phase 16 having an effective permittivity $\in_1$.

As is shown by FIG. 7, the cell 86 used in the calculation has a central axis which extends radially relative to the axis X-X' of the pipe 14 and which extends coaxially with the axis Z-Z' of the central core 56 of the low-frequency probe 50.

The metal wall 88 comprises an inside wall 92 and an outside wall 94 which are substantially flat and have circular contours and which are connected together by a cylindrical peripheral wall 96 of axis Z-Z'. The walls 88, 92 are separated by a distance $h_1$ along the axis Z-Z'.

In the theoretical calculation cell 86, the coaxial probe 50 is flush with the outside wall 94 substantially in the center of the wall 94. Accordingly, the annular dielectric window 62 of the probe 50 is flush, in the theoretical calculation, with the wall 94 so that it is in contact with the liquid phase 16 present in the cell 86.

The radius of the cell, taken about the axis Z-Z', is greater than the radius of the probe 50.

The calculation phase 84 comprises the choice 98 of a particular geometry of the cell 86. That particular geometry of the cell 86 is chosen by comparison between the values of the real and imaginary components of the admittance as a function of the $TM_{01}$-mode frequency in the theoretical cell and in the pipe 14 as simulated by a finite element model for a frequency range from 0 MHz to 2000 MHz.

Figure 6:
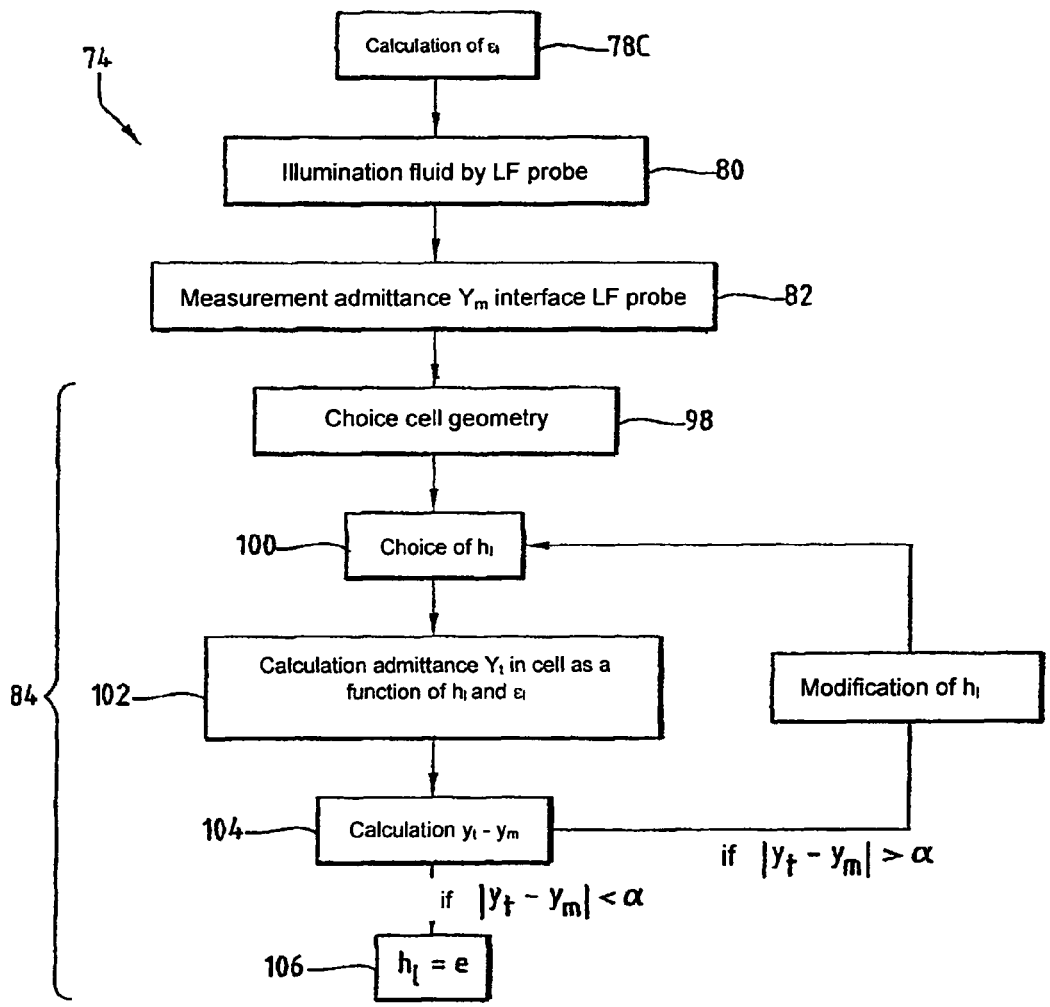
FIG. 6 is a flow chart describing the details of the step of determining the thickness of the liquid phase in the method of FIG. 4.

As is shown by FIG. 6, once the geometry of the cell 86 has been chosen in phase 98, an arbitrary value of the radial dimension $h_1$ of the cell 86, taken along the axis Z-Z' between the walls 92, 94, is chosen in phase 100.

Then, the theoretical admittance $Y_t$ at the interface between the probe 50 and the liquid phase 16 in the calculation cell 86 is calculated in phase 102 by analytical resolution of the propagation of the second electromagnetic wave emitted at frequency $f_b$ in the cell 86 by using the analytical calculations described, for example, in the article by O. Meyer et al., Cellule de Caractérisation Diélectrique Large Bande Surdimensionnée, 7émes Journées Micro-ondes et Matériaux, Toulouse, March 2002.

This step includes the analytical resolution of the Maxwell equations in the geometry of the cell 86 with the limiting conditions defined by the metal walls 88 of the cell 86. This makes it possible to obtain an equation which links the analytically calculated admittance $Y_t$ directly to the dimensions of the cell 86 and to the propagation characteristics of the second electromagnetic wave in the cell 86.

In these calculations, the metal wall 96 located away from the probe 50 is replaced by a magnetic wall.

In phase 104, the absolute value of the difference between the theoretical admittance $Y_t$ and the measured admittance $Y_m$ is calculated. If that difference is greater than a predetermined convergence value α, the radial dimension of the calculation cell 86, taken between the walls 92 and 94, is modified according to a convergence criterion, and phases 102 and 104 of calculation of the theoretical admittance $Y_t$ and of calculation of the difference between $Y_t$ and $Y_m$ are repeated.

In phase 106, when the absolute value of the difference between the theoretical admittance $Y_t$ and the measured admittance $Y_m$ is less than the convergence value α, the thickness of the liquid layer e is considered to be equal to the resulting radial dimension $h_1$ of the calculation cell 86.

Then, in step 76 of calculation of the GHU, the surface $S_1$ of the liquid phase taken in section according to a horizontal plane is calculated from the thickness e of the liquid phase 16.

Likewise, the surface $S_g$ of the gas phase 18, taken in section in the same plane, is calculated by the difference between the surface $S_1$ of the liquid phase 16 and the total surface of the pipe 14 taken in section in the same plane. The GHU is thus determined by the ratio of the surface $S_g$ to the surface $S_1$.

In the invention which has just been described, a high-frequency probe 32 operating at least 25 GHz is used in a first phase in order to measure, easily and in a very selective manner, the composition of the liquid phase 16 of a multiple-phase fluid without taking into account the gas phase 18. In addition, the use of a low-frequency probe 50, supplemented by a resolved analytical calculation of propagation in a calculation cell 86 of simple geometry which differs from that of the pipe 14, makes it possible to obtain simply and very accurately the value of the thickness e of the liquid phase 16 and, consequently, the ratio of the surfaces of the phases 16, 18 flowing through the pipe 14.

The method according to the invention carried out in the device 12 is therefore particularly effective for determining the properties of the multiple-phase fluid without the use of a radioactive probe.

In a variant, the high-frequency probe 22 and the low-frequency probe 24 are located substantially at the same height relative to the pipe 14 in a common vertical plane, offset angularly about the axis X-X' of the pipe 14. In this case, the illumination of the probes 22 and 24 is sequential and not simultaneous.

In another variant, at least one of the dielectric windows 42, 62 is formed by an annular sleeve which surrounds the central core 38, 56. In this case, the end of the central core is flush with the inner face 44, 64 in the pipe 14 and is in contact with the liquid phase 16.

In a variant (not shown), the pipe 14 is substantially horizontal. In this case, the liquid phase 16 covers a lower surface of the pipe 14 delimited at the top by a horizontal plane constituting the interface between the liquid phase 16 and the gas phase 18.

The high-frequency probe 32 and the low-frequency probe 50 are located vertically beneath the pipe 14, spaced along a horizontal lower generatrix of the pipe 14.

The thickness e of the liquid phase 16 is then defined as the distance taken vertically between the lower generatrix and the interface between the liquid phase 16 and the gas phase 18.

The invention claimed is:

1. A method of analyzing a multiple-phase fluid flowing through a pipe, the fluid comprising a liquid phase having at least two constituents in contact with a surface of the pipe and having a gas phase located away from the surface of the pipe, said method comprising:
   (a) determining relative fractions of the two constituents of the liquid phase, said determining of the relative fractions comprising the following sub-steps:
      (a1) illuminating the fluid using a first coaxial probe placed in contact with the liquid phase emitting a first electromagnetic wave at a high frequency;
      (a2) measuring an admittance at an interface between the first coaxial probe and the fluid; and
      (a3) calculating of the relative fractions of the two constituents of the liquid phase based on the measured admittance at the interface between the first coaxial probe and the fluid; and
   (b) determining a thickness of the liquid phase, said determining of the thickness comprising the following sub-steps:
      (b1) calculating an effective permittivity of the liquid phase based on the relative fractions calculated in sub-step (a3);
      (b2) illuminating the fluid using a second coaxial probe separate from the first coaxial probe, the second coaxial probe emitting a second electromagnetic wave at a low frequency;
      (b3) measuring an admittance at the interface between the second coaxial probe and the fluid; and
      (b4) calculating the thickness of the liquid phase based on the calculated effective permittivity of the liquid phase and on the measured admittance at the interface between the second coaxial probe and the fluid.

2. The method of claim 1, wherein the first coaxial probe comprises:
   a central core extending radially relative to an axis of the pipe; and
   a cylindrical solid dielectric window having a first face in contact with the fluid and a second face in contact with the central core, the first electromagnetic wave being emitted through the dielectric window.

3. The method of claim 2, wherein said calculating the relative fractions of the two constituents in the liquid phase comprises establishing a correlation between:
   (i) a simulated admittance at the interface between the first coaxial probe and a reference fluid; and
   (ii) the relative fractions of two constituents of the reference fluid based on a finite element simulation of the propagation of the first electromagnetic wave in the reference fluid.

4. The method of claim 2, wherein the high frequency of the first electromagnetic wave is greater than 25 GHz.

5. The method of claim 4, wherein the high frequency of the first electromagnetic wave is in a range from 30 GHz to 60 GHz.

6. The method of claim 2, wherein the second coaxial probe comprises:
   a central core extending radially relative to an axis of the pipe; and
   a cylindrical solid dielectric window having a first face in contact with the fluid and a second face in contact with the central core.

7. The method of claim 2, wherein the low frequency of the second electromagnetic wave is less than 1 GHz.

8. The method of claim 1, wherein said calculating the relative fractions of the two constituents in the liquid phase comprises establishing a correlation between:
   (i) a simulated admittance at the interface between the first coaxial probe and a reference fluid; and
   (ii) the relative fractions of two constituents of the reference fluid based on a finite element simulation of the propagation of the first electromagnetic wave in the reference fluid.

9. The method of claim 8, wherein the high frequency of the first electromagnetic wave is greater than 25 GHz.

10. The method of claim 9, wherein the high frequency of the first electromagnetic wave is in a range from 30 GHz to 60 GHz.

11. The method of claim 8, wherein the second coaxial probe comprises:
    a central core extending radially relative to an axis of the pipe; and
    a cylindrical solid dielectric window having a first face in contact with the fluid and a second face in contact with the central core.

12. The method of claim 1, wherein the high frequency of the first electromagnetic wave is greater than 25 GHz.

13. The method of claim 12, wherein the high frequency of the first electromagnetic wave is in a range from 30 GHz to 60 GHz.

14. The method of claim 12, wherein the second coaxial probe comprises:
    a central core extending radially relative to an axis of the pipe; and
    a cylindrical solid dielectric window having a first face in contact with the fluid and a second face in contact with the central core.

15. The method of claim 1, wherein the second coaxial probe comprises:
    a central core extending radially relative to an axis of the pipe; and
    a cylindrical solid dielectric window having a first face in contact with the fluid and a second face in contact with the central core.

16. The method of claim 1, wherein the low frequency of the second electromagnetic wave is less than 1 GHz.

17. The method of claim 1, wherein said calculating the thickness of the liquid phase comprises using an equation linking:
    (i) a theoretical admittance calculated at an interface between the second coaxial probe and a theoretical calculation cell having a finite radial length and a geometry different from that of the pipe; to
    (ii) the calculated effective permittivity of the liquid phase; and
    (iii) the radial length of the theoretical calculation cell;

wherein the equation is obtained based on the analytical resolution of a mathematical model of propagation of the second electromagnetic wave in the theoretical calculation cell.

18. The method of claim 17, wherein said calculating the thickness of the liquid phase further comprises:

varying the radial length of the theoretical calculation cell;

calculating a difference between (i) an admittance calculated based on a mathematical model of propagation in the theoretical calculation cell at the interface between the second probe and the fluid, and (ii) the admittance at the interface between the second coaxial probe and the fluid as measured in sub-step (b3); and determining the thickness of the liquid phase based on the radial length of the theoretical calculation cell obtained when the difference is less than a predetermined value.

19. The method of claim 17, wherein the theoretical calculation cell is formed of a closed hollow metal cylinder having a radial axis coaxial with an axis of a central core of the second probe, the closed hollow metal cylinder having a first transverse wall located at the interface between the second coaxial probe and the pipe, the radial length of the theoretical calculation cell being a distance separating the first transverse wall and a second transverse wall delimiting the closed hollow metal cylinder.

20. A device for analyzing a multiple-phase fluid flowing through a pipe, the fluid comprising a liquid phase having at least two constituents in contact with a surface of the pipe and having a gas phase located away from the surface of the pipe, said device comprising:

(a) a determining means for determining relative fractions of the two constituents of the liquid phase, said means comprising:

(a1) a first coaxial probe for contacting the liquid phase and configured to emit a first electromagnetic wave at a high frequency;

(a2) a first measuring means for measuring an admittance at the interface between said first coaxial probe and the fluid; and (a3) a first calculating means for calculating the relative fractions of the two constituents in the liquid phase based on the measured admittance at the interface between said first coaxial probe and the fluid measured by said first measuring means; and (b) a thickness determining means for determining a thickness of the liquid phase, said means comprising:

(b1) a permittivity calculating means for calculating an effective permittivity of the liquid phase based on the relative fractions calculated by said first calculating means for calculating the relative fractions of the two constituents in the liquid phase;

(b2) a second coaxial probe separate from said first coaxial probe, said second coaxial probe being configured to emit a second electromagnetic wave at a low frequency;

(b3) a second measuring means for measuring an admittance at an interface between said second coaxial probe and the fluid; and (b4) a second calculating means for calculating the thickness of the liquid phase based on the effective permittivity calculated by said permittivity calculating means, and based on the measured admittance at the interface between said second coaxial probe and the fluid measured by said second measuring means.

21. The device of claim 20, wherein said first coaxial probe comprises:

a central core extending radially relative to an axis of the pipe; and a cylindrical solid dielectric window having a first face to contact the fluid and a second face contacting said central core.

22. The device of claim 20, wherein said second coaxial probe comprises:

a central core extending radially relative to an axis of the pipe; and a cylindrical solid dielectric window having a first face to contact the fluid and a second face contacting said central core.

23. The device of claim 20, wherein said thickness determining means is configured to use an equation linking:

(i) a theoretical admittance calculated at an interface between said second coaxial probe and a theoretical calculation cell having a finite radial length and a geometry different from that of the pipe; to (ii) the calculated effective permittivity of the liquid phase; and (iii) the radial length of said theoretical calculation cell;

wherein the equation is obtained based on the analytical resolution of a mathematical model of propagation of the second electromagnetic wave in said theoretical calculation cell.

* * * * *